(12) United States Patent
Ikeda

(10) Patent No.: US 7,087,032 B1
(45) Date of Patent: Aug. 8, 2006

(54) CONTROLLING UNDERGARMENT

(76) Inventor: Chieko Ikeda, 591-11, Shimoyata, Nakatara, Maihara-cho, Sakata-gun, Shiga 521-0011 (JP)

( * ) Notice: Subject to any disclaimer, the term of this patent is extended or adjusted under 35 U.S.C. 154(b) by 0 days.

(21) Appl. No.: 11/074,248

(22) Filed: Mar. 7, 2005

(51) Int. Cl.
*A61F 5/00* (2006.01)

(52) U.S. Cl. .............................. 602/19; 128/891; 2/409; 450/150

(58) Field of Classification Search .................. 602/19; 2/408, 78.2, 409, 238, 69, 228, 227; 450/100–103, 450/98, 123, 154, 106, 109, 112–114, 130, 450/131, 151
See application file for complete search history.

(56) References Cited

U.S. PATENT DOCUMENTS

| | | | | |
|---|---|---|---|---|
| 2,908,277 A | * | 10/1959 | Peck | 450/101 |
| 3,777,764 A | * | 12/1973 | Herbener | 450/95 |
| 5,930,838 A | * | 8/1999 | Carter-Scott-Pomije | 2/79 |
| 5,954,564 A | * | 9/1999 | Ganz | 450/99 |

FOREIGN PATENT DOCUMENTS

| | | |
|---|---|---|
| JP | 8-60407 | 3/1998 |
| JP | 10-212606 | 8/1998 |
| JP | 2002-209921 | 7/2002 |

\* cited by examiner

*Primary Examiner*—Henry Bennett
*Assistant Examiner*—Shumaya B. Ali
(74) *Attorney, Agent, or Firm*—Milde & Hoffberg, LLP

(57) ABSTRACT

The present invention provides a controlling undergarment covering a wearer's abdomen, lumbar, and thigh capable of stabilizing the pelvis, tightening the swelling of the center of the abdomen, and performing a correction to stabilize the lower buttocks without discomfort and the need for putting on and taking off when excreting which comprises: a main body for covering the wearer's abdomen, lumbar, and thigh composed by the connection of a front part, a back part, and two leg parts; and a belt with stretchability for surrounding the front and back sides of the main body wherein a crotch region is open.

7 Claims, 3 Drawing Sheets

CONTROLLING UNDERGARMENT

BACKGROUND OF THE INVENTION

1. Field of the Invention

The present invention relates to a controlling undergarment for covering a wearer's abdomen, lumbar, and thigh. More particularly, the invention provides a controlling undergarment which is capable of stabilizing the pelvis, tightening the swelling of the center of the abdomen, controlling the swelling of the abdomen, and performing a correction to stabilize the lower buttocks without discomfort, as well as being a controlling undergarment without the need for putting on and taking off when excreting.

2. Description of Related Art

A desire to maintain more beautiful posture and shape is common to all age groups of women. Controlling the body to a certain extent is rather helpful for movements of a wearer than leaving bulges of flesh as they were. Further, applying a certain extent of external pressure to the abdomen and the lumbar effectively works in making smooth movements by enhancing soft muscles and stabilizing the position of the pelvis.

Girdles are used for such purposes. Conventional girdles generally correct the wearer's lumbar and abdomen by the application of non-stretchable partial clothes or low stretchable partial clothes having good shrinkability to the center of the abdomen, the lower buttocks, and the waist to correct the wearer's abdomen, lumbar, and buttocks by tightening bulges of flesh in the abdomen and the buttocks as well as the lumbar (For example, Japanese Patent Application No. JP08-60407 or Japanese Patent Application No. JP10-212606).

Recently, a variety of orthopedic belts have been suggested to correct the position of bones, such as the pelvis that causes various diseases of the body (For example, see Japanese Patent Application No. 2002-209921).

These are generally belt-shaped covering from the hipbones to the pelvis of the wearer and are fixed with a surface fastener.

In the case of putting on and taking off a conventional girdle, however, a fixed force and time are needed to put on and take off the girdle by taking the trouble to stretch a cloth which is partially non-stretchable or low stretchable included in the girdle.

Putting on and taking off a girdle becomes a burden especially on people who have weak muscle strength, sickly people, and middle and aged people. Although it is necessary for them to put on and take off the underwear quickly when excreting, they tend to avoid wearing a girdle because it takes time to wear the girdle as mentioned above. They tend to become negative about wearing the girdle when going out or traveling because it takes time to put on and take off the girdle when excreting, although wearing the girdle tightens the figure of the wearer.

When the above-mentioned conventional orthopedic belt is worn, the wearing position is displaced at the lapse of time by the mode of behavior, walking, and exercising. In addition, troublesome work is needed to return to the normal position lest the wearer should be bothered in smooth exercise.

Accordingly, the development of girdles which are easy to wear and rectify the position of the wearer has been demanded.

As a result of devoted research on the development of a controlling undergarment, we have attained the present invention that solves problems with the above-mentioned conventional girdles and orthopedic belts targeted for all age groups which is capable of easily putting on and taking off so that the wearer can positively enjoy her daily life or trip and contributing to body contouring and pelvis correcting.

SUMMARY OF THE INVENTION

A controlling undergarment according to the present invention comprises: a main body for covering a wearer's abdomen, lumbar, and thigh composed by the connection of a front part, a back part, and two leg parts; and a belt with elasticity surrounding the front part and the back part of the main body, wherein the main body protects the wearer's abdomen, lumbar, and thigh from differences in outdoor temperature and external stimulus, and then applies a stretching force of the belt to the wearer's body up to the appropriate degree. The front part, the back part, and the leg parts connected in the main body are characterized in that a crotch portion is always open. It does not take time so long to put on and take off a girdle because the wearer can excrete by taking off only an underwear when first wearing a controlling undergarment of the present invention and then wearing the underwear.

The belt is provided at least on (1) a line to connect the upper portion of the left and right hipbones in the wearer's lumbar, (2) lines to cross at the center of the abdomen extending from the upper portion of the left and right hipbones to respective joints between the lower portion of the right and left pelvis and the thighbones, and (3) darts under left and right buttocks, and (4) lines extending from the inner groin side of left and right thighs to the vicinity of the navel via the left and right groin in the front part and the back part of the main body, and surrounds the wearer's abdomen and lumbar to effectively tighten the distended regions of the abdomen and the buttocks to be secured.

Although the main body covers from the wearer's upper hipbones to the lower abdomen and lumbar, the main body does not compress the abdomen because of no coverage of the waist region.

The belt effectively tightens bulges of flesh in the wearer's abdomen and lumber to be secured because the belt is made of a material having stretchability in a longitudinal direction.

The wearer's movement from the legs to the buttocks becomes more natural and smooth by the forming of stretch gathers that may form distended parts of the buttocks in the back part on the whole of or a part of the main body positioned in the posterior rugae connecting the vicinity of the sacrum and the vicinity of the lumbar vertebrae.

Further, the belt is consisted of one belt-type body and the unsecured belt part is capable of moving as the wearer wishes by being secured at least to a center of the upper back part and central edges of the upper front part, which enables freely changes in looseness and tightness of the belt.

The width of the belt is favorably in a range from 2 cm to 8 cm, which results in effective body shaping and correcting.

The term "wearer" used herein means a general public regardless of sex who have a variety of builds and figures generally use girdles.

BRIEF DESCRIPTION OF THE DRAWINGS

FIG. 1(a) is a front view and FIG. 1(b) is a back view.

DESCRIPTION OF THE PREFERRED EMBODIMENTS

The present invention will now be described in detail below in the accompanying drawings.

Figure 1:
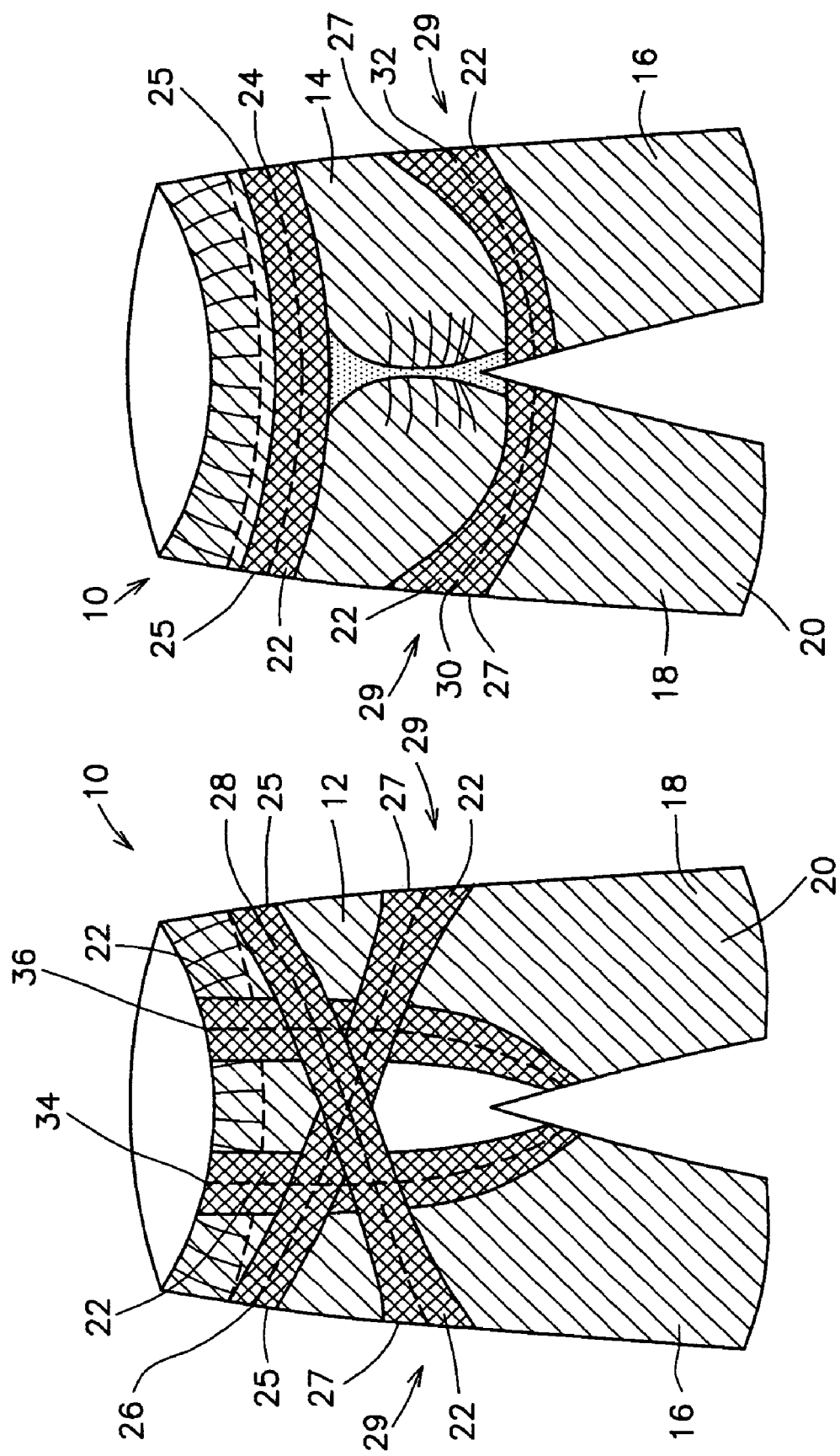
FIGS. 1(a) and 1(b) are respectively schematic views of examples of a controlling undergarment according to the present invention.

FIGS. 1(a) and 1(b) are respectively partial schematic views of a controlling undergarment 10 according to the present invention. FIG. 1(a) shows a front of a wearer's abdomen and lumbar. FIG. 1(b) shows a back of the wearer's abdomen and lumbar. The controlling undergarment 10 of the present invention has a shape covering the wearer's abdomen, lumbar, and thigh. The controlling undergarment 10 comprises: a main body 20 for covering the wearer's abdomen, lumbar, and thigh configured by the connecting of a front part 12, a back part 14, and two leg parts 16 and 18; and a belt 22. The belt described herein is in a stretched state by being worn by the wearer.

The belt 22 is provided by surrounding the front part 12 and the back part 14 of the main body 20. More specifically, the belt 22 is provided on (1) a line 24 to connect the upper portion of the left and right hipbones in the wearer's lumbar of the back part 14, (2) two lines 26 and 28 to cross at the center of the abdomen extending from the upper portion of the left and right hipbones to respective joints between the lower portion of the right and left pelvis and the thighbones in the front part 12, (3) darts 30 and 32 under left and right buttocks, and (4) lines 34 and 36 extending from the inner groin side of the left and right thigh to the vicinity of the navel along the left and right groin in the main body 20. The belt is provided on a line connecting from the above-mentioned lines (1) to (4).

When a belt is provided on (1) the line 24 to connect the upper portion of the left and right hipbones in the wearer's lumbar of the back part, a uniform external force caused by the stretchability of the belt 22 is applied to the pelvis, which results in effects for steady securing and straightening of the pelvis.

And bulges of flesh in the center of the wearer's abdomen can be tightened by providing the belt 22 on (2) the lines 26 and 28 to cross at the center of the abdomen extending from the upper portion of the left and right hipbones to respective joints between the lower portion of the right and left pelvis and the thighbones. In the bulged part at the center of the abdomen, there may be swelling of intestines due to bulges of flesh including subcutaneous fat as well as pendulous viscera and may exert such effect that these viscera return to in place.

Connections 25 between the above-mentioned (1) and (2), that is, the region of the belt 22 in the upper portion of the left and right hipbones has the effect of controlling excess weight which is easy to put on around the upper hipbones.

Providing the belt 22 on (3) the darts 30 and 32 under the left and right buttocks in the back part 14 makes it possible to pull up flesh that is easy to fall down in the lower buttocks, which leads to shaping the hip line. Further, securing muscle in the lower buttocks eases an uncomfortable feeling that the stiff part of a chair touches the bones when sitting on a chair, so that it is possible to sit on a chair comfortably for a long time. For example, the controlling undergarment of the present invention is suitable for middle and aged people whose muscle is becoming weaker.

Connections 27 between the above-mentioned (2) and (3), that is, the belt region that is analogous to joints 29 between the lower portion of the left and right pelvis and the left and right thighbones has the effect of protecting these joints.

Providing the belt 22 on (4) lines 34 and 36 extending from the inner groin side of the left and right thighs in the front part 12 to the vicinity of the navel along the left and right groin can stimulate the lymphatic flow, which results in the looping of the belt 22 around the left and right groin lymph nodes respectively due to the movement of the belt 22 made according to the wearer's movement.

Both ends of the belt 22 in the center of the abdomen of the front part on the line (4) are secured by a fastening means (not shown in FIGS. 1(a) and 1(b)) to a part of an end of the girth of the abdomen in the front part of the main body.

A variety of materials may be selected as a belt used for the controlling undergarment of the present invention. For example, materials having unidirectional or two-directional elasticity are preferably used and non-stretchable materials are also preferably used for the controlling undergarment of the present invention. Stretchable materials are generally preferable, materials having streatchability in a longitudinal direction are especially preferable. Examples of the materials include power net, two-way tricot, marqueezetto, and tricot or greatly elasticized materials using elastic fibers and textured yarn.

The width of the belt is preferably from 2 to 8 cm. The belt bites into the wearer's body as well as the tightening and correcting effects exert only in a narrow area when the belt has a width of less than 2 cm, which is not preferable. On the contrary, the belt covers nearly the whole area of the wearer's abdomen and lumbar when the belt has a width of over 8 cm, which may disturb the movements of the wearer.

It is also possible to change the width of the belt according to the portion that the belt touches within the above-mentioned range. For example, (1) a belt positioned in the lumbar connecting the hipbones and/or (2) a belt positioned on the line 26 to cross at the center of the abdomen extending from the upper portion of the left and right hipbones to the joints between the lower portion of the right and left pelvis and the thighbones respectively may have a relatively wide width, and (3) a belt provided on the darts 30 and 32 under the left and right buttocks and/or (4) a belt provided on the lines 34 and 36 extending from the inner groin side of the left and right thighs to the vicinity of the navel along the left and right groin may have a relatively narrow width. Thus, the controlling undergarment according to the present invention is capable of effectively tightening bulges of flesh in the lumbar and abdomen in a relatively wide range, as well as enabling to locally and effectively lift up the flesh in the lower buttocks and effectively stimulate the groin lymph node.

The belt may be either secured to the main body in all faces or may partially be secured to the main body from the above-mentioned positions (1) to (4). In this case, the belt may be previously incorporated into the above-mentioned position in the sewing or the bonding or the manufacturing process of the main body as a part of the main body. The belt may be respectively provided as long as the belt is provided at the above-mentioned positions.

Intersections of the above-mentioned belt may be the upper portion of any parts of the crossing belt.

To adjust the belt respectively to the wearer's body having a variety of physical features while effectively shaping and correcting the body, it is preferable that the belt maintains flexibility which freely varies tightness and looseness and the places to be provided. Accordingly, the belt surrounding the main body is preferably one belt.

More specifically, one end and another end of the belt are respectively secured to the left and right of the central edges in the upper front part. And the belt forms one band extending from one end to another end via on darts formed under left buttock from the left groin to the inner groin side of the left thigh, lines to connect the joint between the lower portion of the left pelvis and the thighbone, the upper portion of the right hipbone in the lumbar, and the upper portion of the right and left hipbones in the lumbar of the back part, darts formed under right buttock from the upper portion of the left hipbone in the lumbar to the joint between the lower portion of the right pelvis and the thighbone, and a line extending from the inner groin side of the right thigh to the vicinity of the navel via the right groin.

Figure 2:
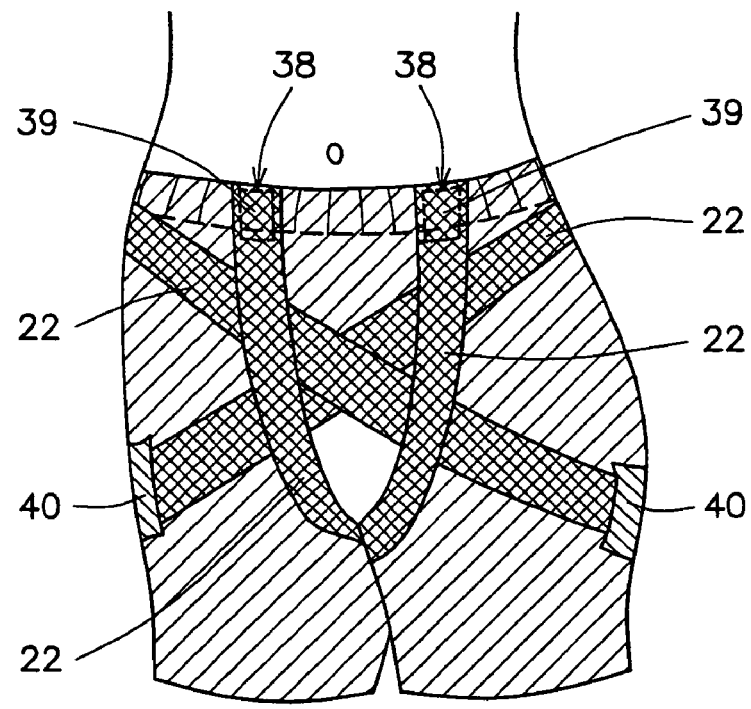
FIG. 2 is a front view illustrating another example of the controlling undergarment according to the present invention.
Figure 3:
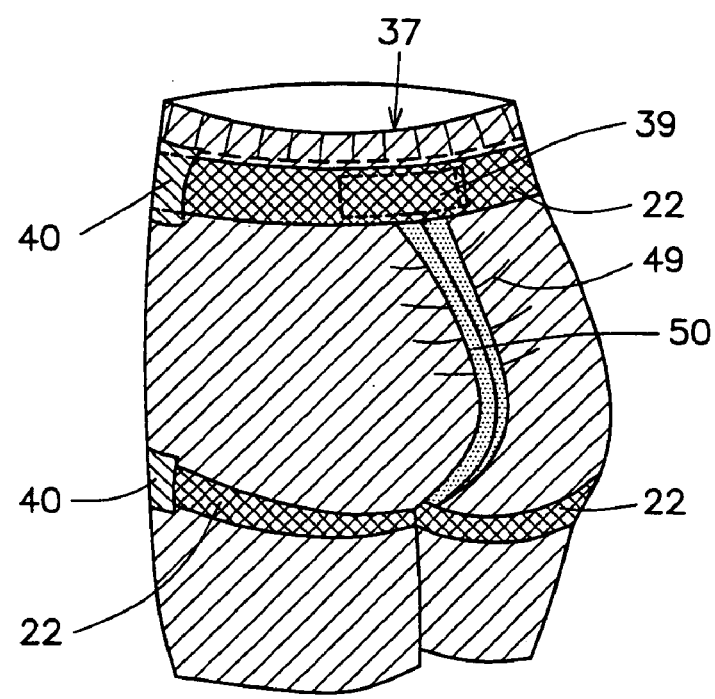
FIG. 3 is a back view illustrating still another example of the controlling undergarment according to the present invention.

In this case, as is shown in FIGS. 2 and 3, the belt 22 is secured at least to a center 37 of the upper back part, and central edges 38 of the upper front part in the main body by a fastening means 39. More specifically, as shown in FIG. 3, the center of the length of the belt is secured to the center 37 of the upper back part and as shown in FIG. 2, both ends of the belt are secured to the central edges 38 of the upper front part. By doing this, the unsecured belt can select between the most suitable position within the range of the position to be provided and the placement of the belt with flexibility in elasticity while maintaining the belt within the above-mentioned range of positions (1) to (4) to be provided.

A fastening means may be used alone or in a combination of attachable and detachable catching means, such as snaps, buttons, and surface fasteners or the like as well as securing by sewing or bonding or the like. It is preferable to provide a plurality of snaps and buttons attached to the belt in the direction of the length of the belt and have an adjuster function as a gender surface fastener with certain area when catching means are used so that the length of the belt can be adjusted according to the build and figure or the taste of the wearer. FIGS. 2 and 3 respectively show a fastening means 39 by sewing.

In addition, belt lead means may be provided at predetermined places in the main body. It is preferable that this enables the belt to have flexibility in tightness and looseness while leading the belt to a predetermined position. More specifically, as shown in FIGS. 2 and 3, lead means 40, such as yarn, strings, and bands for leading the belt are provided at a plurality of places in the main body.

Figure 4:
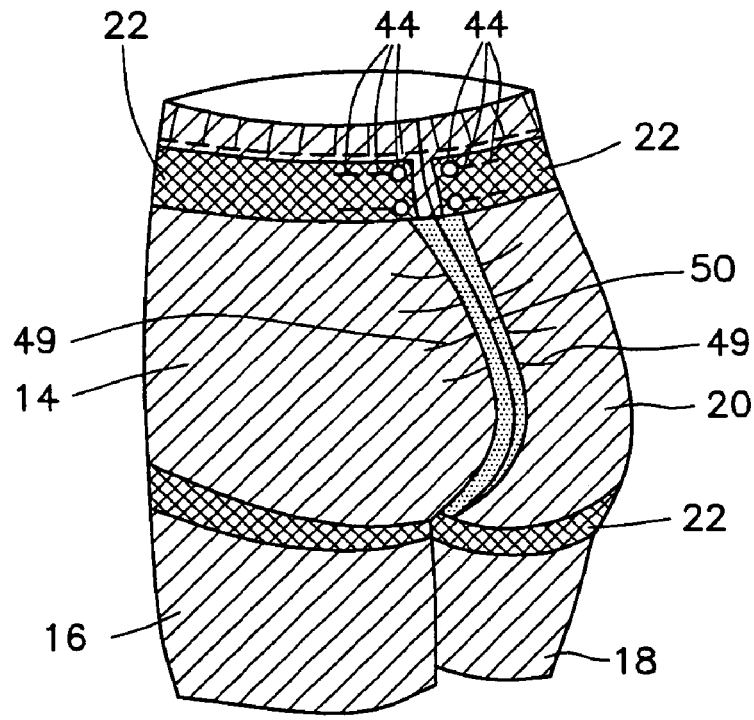
FIG. 4 is a back view illustrating a further example of the controlling undergarment according to the present invention.

Alternatively, as shown in FIG. 4, a pair of belts may be used and one of the belts may respectively have an adjuster function at their both ends in combination with attachable and detachable catching means 44 in the lumbar of the back part and the ends of the belts. In FIG. 4, catching means are a plurality of buttonholes provided at the ends of the belt and buttons provided on the main body. Such adjuster function may also be provided at the center ends in the lumbar of the front part of the belt, although that is not shown in figures. In this case, even the belt is in the form of one belt, it may have an adjuster function on both ends of the belt as a set of 2 belts.

Figure 5:
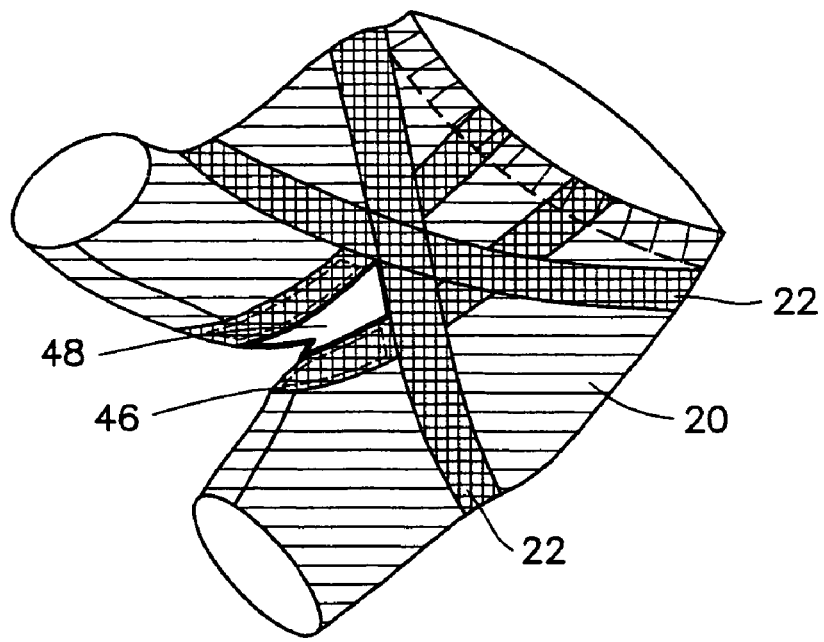
FIG. 5 is a view illustrating a still further example of the controlling undergarment according to the present invention.

The belt fastening means and the belt lead means may be provided at any places pin the main body within the range of the above-mentioned (1) to (4). For example, the belt region from the left and right groin to the lower portion of the left and right buttocks has each end at a place corresponding to the front part, the back part, and the leg parts to open a crotch region which is a connection between the leg parts and the body. As shown in FIG. 5, when the position of the belt is fixed at the ends of this region by a fastening means or a belt lead means, it is preferable that ends of each part become reinforced and bites into the wearer's body are reduced at the time of movements. The belt fastening means is a fastening means 46 by sewing in FIG. 5.

As shown in FIG. 5, the controlling undergarment according to the % present invention is characterized in that its crotch portion is not joined but is opened, although the front part 12 and the back part 14 in the main body 20 meet at a side line and the front part 12 and the leg parts 16 and 18 following the back part meet at the crotch region. The shape of an opening 48 is not limited as long as it includes the crotch region. The place surrounded by a thick line in FIG. 5 shows the opening 48. In FIG. 3, the opening 48 is formed by surrounding with the belt 22 and the shape of this part is secured by fixing the belt, which leads to a contribution to smooth movements of the wearer's behavior.

In conventional girdles, a crotch region cloth is always added when sewing the front part, the back part and the leg parts and acts as a role of making more smooth movements of the wearer's legs.

However, troublesome work has been needed to put on and take off a conventional girdle every time performing an excretion because there is a crotch region including a crotch cloth in the girdle.

In the controlling undergarment according to the present invention, a region where a crotch cloth was originally applied is opened by removing the crotch region. Accordingly, excretion is possible by putting on and taking off the underwear put on the controlling undergarment without the need for putting on and taking off the controlling undergarment of the present invention by previously wearing an underwear before wearing the controlling undergarment of the present invention when excreting. It is possible to put on and take off the underwear smoothly in a short time without the repetition of troublesome work.

A variety of shapes may be selected as the main body 20 as far as providing a belt as mentioned above and covering the wearer's abdomen, lumbar, and thigh. The greater improvement of stretchability in the ends of the abdomen and the ends of leg parts than other regions makes the controlling undergarment fit better the wearer's body, which is preferable. The center of the thigh, the upper knees, and the lower knees or the like may be selected as the length of the ends of the leg parts. A variety of materials may be used for the main body 20. These material may have unidirectional or two-directional elasticity or may be non-stretchable. Examples of stretchable materials include: jersey, smoothness, T-cloth, and two-way tricot or the like, and materials including elastic fibers, such as polyurethane fibers and finished yarn, such as spring yarn.

As shown in FIG. 2, in the controlling undergarment according to the present invention, the main body 20 covers from the upper pelvis to the lower abdomen and the lumbar of the wearer, but it is preferable that the main body 20 does not cover the waist because the controlling undergarment can be worn comfortably for a long time without discomfort due to no tightening in the waist even the abdomen is swelled by having a meal because of external pressure applied.

Further, in the controlling undergarment according to the present invention, stretch gathers which may form bulges of the buttocks in the back part when wearing the controlling undergarment are preferably formed on the whole of or a part of the main body positioned in the posterior rugae connecting the vicinity of the sacrum and the vicinity of the lumbar vertebrae. For example, as shown in FIGS. 3 and 4, stretch gathers 49 are formed in the posterior rugae of the main body connecting between the vicinity of the sacrum and the vicinity of the lumbar vertebrae of the wearer by providing an elastic member in that region. In these figures, the controlling undergarment according to the present invention is worn and the gathers 49 are in a state of stretching along the wearer's body. The formation of the stretch gathers 49 enables stretching in the posterior rugae while forming bulges in the left and right buttocks of the main body resulting in the effective fit of the controlling undergarment of the present invention to the wearer's body without discomfort and smooth movements of the wearer's buttocks and legs when used. An elastic member 50 is used to form the stretch gathers in figures, but stretchability may be secured by sewing the above-mentioned specified region using stretchable yarn when forming the back part.

A variety of materials may be used in this case. For example, either unidirectional or two-directional stretchable materials or non-stretchable materials may be used. Stretchable materials are generally preferable. Examples of elastic members include a power net, a two-way tricot, a marqueezertte, and a tricot or the like. This elastic member 50 may be sewed, bonded, and incorporated in the center of the back part 14 of the main body as part of the main body. The effect of reinforcing ends of an opening is also obtained by using such elastic member 50.

The controlling undergarment according to the present invention can be suitably worn by a wide range of age groups, especially women and is effective in shaping the wearer's abdomen and lumbar, correcting bones, such as the pelvis, and protectinq the hip joint and the like as well as having no need for putting on and taking off when excreting.

There has thus been shown and described a novel controlling undergarment thereof which fulfills all the objects and advantages sought therefor. Many changes, modifications, variations, combinations, and other uses and applications of the subject invention will, however, become apparent to those skilled in the art after considering this specification and accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A controlling undergarment for covering a wearer's abdomen, lumbar, and thigh, comprising:
   a main body for covering the abdomen, the lumbar, and the thigh composed by the connection of a front part, a back part, and two leg parts; and
   a belt for surrounding at least a part of the main body, wherein the belt is provided on (1) a line to connect the upper portion of left and right hipbones in the lumbar of the back part, (2) lines to cross at the center of the abdomen extending from the upper portion of the left and right hipbones in the lumbar to respective joints between the lower portion of the right and left pelvis and the thighbones, (3) darts under left and right buttocks, and (4) lines extending from the inner groin side of left and right thighs to the vicinity of the navel via the left and right groin.

2. A controlling undergarment for covering a wearer's abdomen, lumbar, and thigh, comprising:
   a main body for covering the abdomen, the lumbar, and the thigh composed by the connection of a front part, a back part, and two leg parts; and
   a belt for surrounding at least a part of the main body, wherein a crotch portion where the front part, the back part and the two leg parts of the main body are connected at the wearer's crotch region is open, said belt being provided on (1) a line to connect the upper portion of the left and right hipbones in the lumbar of the back part, (2) lines to cross at the center of the abdomen extending from the upper portion of the left and right hipbones in the lumbar to respective joints between the lower portion of the right and left pelvis and the thighbones, (3) darts under left and right buttocks, and (4) lines extending from the inner groin side of the left and right thighs to the vicinity of the navel via the left and right groin.

3. A controlling undergarment according to claim 1, wherein the garment covering a wearer's abdomen, lumbar, and thigh, wherein
   a main body for covering the abdomen, the lumbar, and the thigh composed by the connection of a front part, a back part, and two leg parts; and a belt for surrounding at least a part of the main body, wherein a crotch portion, where the front part, the back part, and the two leg parts of the main body are connected at the wearer's crotch region, is always open, wherein said main body covers a wearer's abdomen and lumbar downward from the upper part of the pelvis except the waist.

4. A controlling undergarment according to claim 1, wherein the garment covering a wearer's abdomen, lumbar, and thigh, wherein
  a main body for covering the abdomen, the lumbar, and the thigh composed by the connection of a front part, a back part, and two leg parts; and
  a belt for surrounding at least a part of the main body, wherein a crotch portion, where the front part, the back part, and the two leg parts of the main body are connected at the wearer's crotch region, is always open, wherein stretch gathers forming bulges of the buttocks in the back part when wearing the controlling undergarment are formed on at least a part of said main body positioned in the posterior rugae connecting the vicinity of the sacrum and the vicinity of the lumbar vertebrae.

5. A controlling undergarment for covering a wearer's abdomen, lumbar, and thigh, comprising:
  a main body for covering the abdomen, the lumbar, and the thigh composed by the connection of a front part, a back part, and two leg parts; and
  a belt for surrounding at least a part of the main body, wherein said belt is composed of one belt-type body and is secured at least to (1) a center of the back part on a line to connect the upper portion of the left and right hipbones in the lumbar of the back part and (2) central edges of the upper front part on lines extending from the inner groin side of the left and right thighs to the vicinity of the navel via the left and right groin.

6. The controlling undergarment according to claim 5, wherein said belt is secured to said main body by a attachable and detachable fastening means.

7. The controlling undergarment according to claim 5, wherein one end and another end of said belt are respectively secured to the left and right of the central edges in the upper front part, said belt extending from the one end to the another end via on darts formed under left buttock from the left groin to the inner groin side of the left thigh, lines to connect a joint between the lower portion of the left pelvis and the thighbone, the upper portion of the right hipbone in the lumbar, and the upper portion of the right and left hipbones in the lumbar of the back part, darts formed under right buttock from the upper portion of the left hipbone in the lumbar to a joint between the lower portion of the right pelvis and the thighbone, and a line extending from the inner groin side of the right thigh to the vicinity of the navel via the right groin.

\* \* \* \* \*